United States Patent [19]
Yanase

[11] 3,977,405
[45] Aug. 31, 1976

[54] BREAST PUMP

[76] Inventor: Shozaburo Yanase, 2-20, Tsurigane-cho, Higashi, Osaka, Japan

[22] Filed: Apr. 7, 1975

[21] Appl. No.: 565,670

[52] U.S. Cl. ............................................. 128/281
[51] Int. Cl.² ........................................... A61M 1/06
[58] Field of Search ........... 128/280, 281, 282, 2 F, 128/DIG. 5, 297–301, 219, 220, 230, 235, 237, 238, 218 R, 218 P, 218 PA, 150, 461; 215/11; 73/423 R, 425, 425.2, 425.4 R, 425.6; 119/14.23, 14.43.14.47, 14.48, 14.49

[56] References Cited
UNITED STATES PATENTS

| | | | |
|---|---|---|---|
| 3,530,979 | 9/1970 | Merrill, Jr. et al. | 215/11 C |
| 3,886,928 | 6/1975 | Sarstedt | 128/2 F |

FOREIGN PATENTS OR APPLICATIONS

| | | | |
|---|---|---|---|
| 1,091,809 | 11/1954 | France | 128/281 |
| 1,179,487 | 1/1970 | United Kingdom | 128/2 F |

*Primary Examiner*—Robert W. Michell
*Assistant Examiner*—Henry S. Layton

[57] ABSTRACT

A breast pump comprises an outer cylinder having an open and closed ends, an inner cylinder having two open ends and adapted to be inserted into said outer cylinder and displaced therein and a packing for sealing a clearance between said outer and inner cylinders.

3 Claims, 10 Drawing Figures

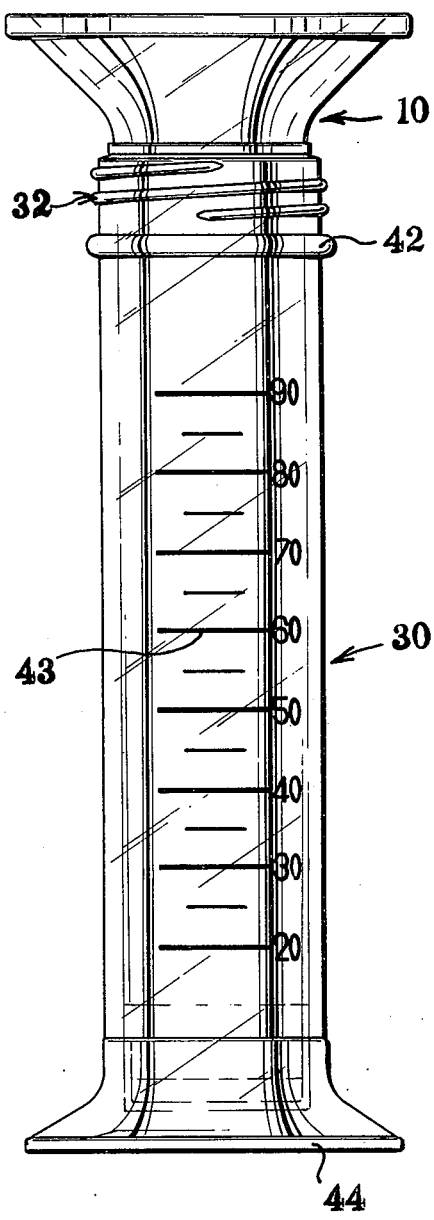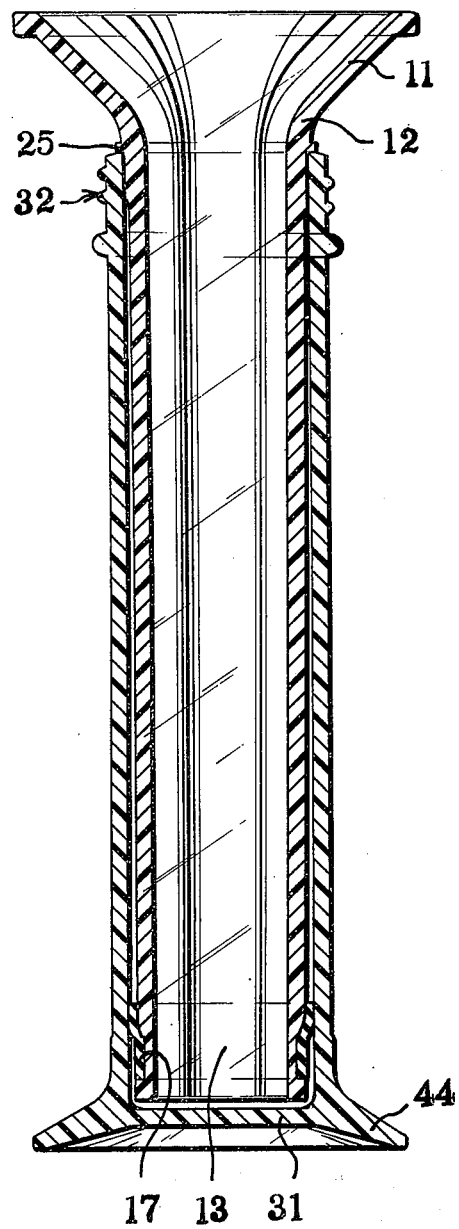

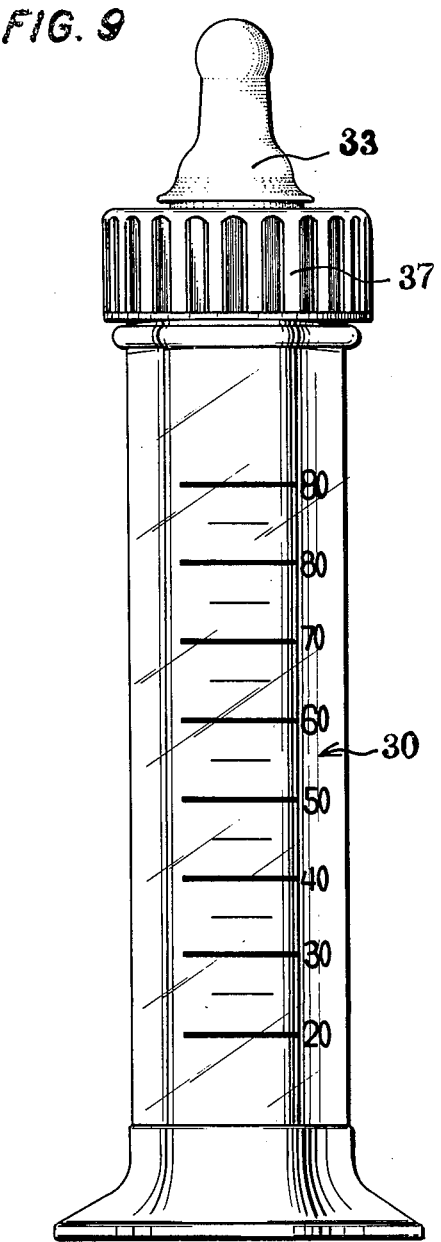
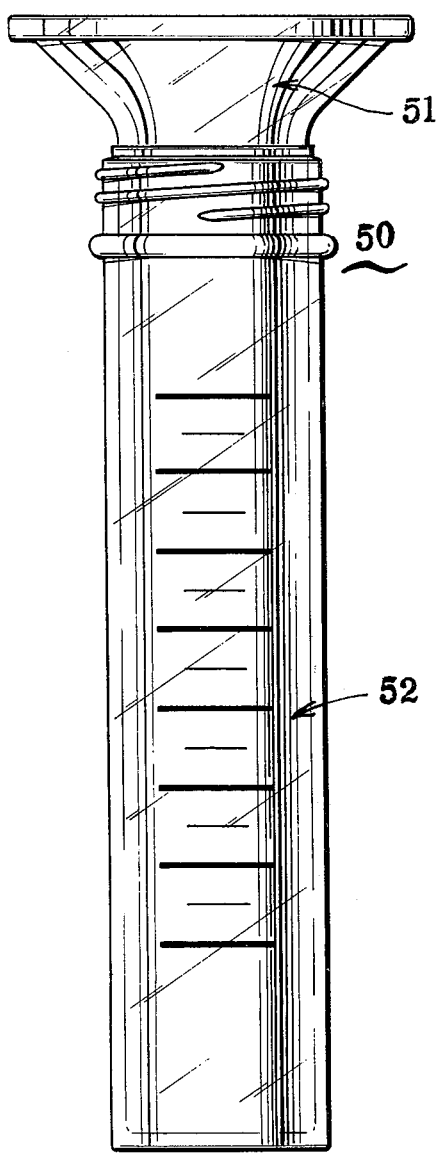

BREAST PUMP

The present invention relates to a breast pump, especially to a breast pump capable of being sterilized so as to feed a baby with mother's milk directly after thereby drawing out the same from the breast.

Mother's milk is indispensable for growing up a baby. Artificial milk can be also fed to a baby instead of mothers's milk. But it is generally proved that a breast-fed baby and a bottle-fed baby are different in their resisting power to disease, that is, the former is stronger than the latter. Further, when suckled at its mother's breast a baby is in touch with its mother's skin. And it has been also proved that the repetition of such touch with mother's skin can make a baby grow to be a child having balanced feeling.

Though maternal feeding has an extremely good influence on a baby's body and heart as abovementioned, artificial feeding is more popular than maternal feeding in general. This fact is the point for us to see. It is considered that maternal feeding is not adopted due to the problems of mother's beauty, her excessive business or other various reasons. But it is also regarded as an essential reason therefor that any breast pump convenient to use has not been developed yet.

At the time of delivery only an extremely small amount of mother's milk is secreted, and the amount increases as days go by. However, a newborn baby has only a feeble sucking force and therefore is not satisfied with its mother's breasts from which only a small amount of milk is secreted even by its sucking with effort. Then, the baby cries for more milk and mother is apt to feed it with artificial milk. To make the matter worse, if efforts are not made to milk mother's breasts at this time of a little secretion obtained only by strong squeezing the same, the successive secretion decreases, finally causing a perfect stop of secretion. It is also generally known that a mother whose breasts have not been sufficiently milked after delivery is slow in her recovery. Therefore this period is very important for mother and her baby to make efforts to milk the breasts.

Furthermore, even if such efforts are made in this period and mother's milk is successively secreted, such secretion easily ceases by afterward interrupting milking e.g. when illness separates a baby from its mother.

However, such a problem can be easily solved by providing a convenient breast pump.

A conventional breast pump comprises a suction tube having one divergent end and provided at the other end with a rubber ball. In this conventional breast pump, milking is effected by exhausting the air in the ball to outside, then closely contacting the divergent open end about a teat and drawing out mother's milk using restoration force of the rubber ball. In a breast pump of this type, since mother's milk is drawn out by means of restoration force of a rubber ball as abovementioned, the amount drawn out at one time is small and the open end of the suction tube has to be separated every one time so as to exhaust air. Therefore, this breast pump is inconvenient to use and besides, drawn milk is apt to flow out during exhausting air. Decisive disadvantages of a breast pump of this type are that harmful material is eluted from the rubber ball and that drawn mother's milk has to be thrown away because it is not intended to be sterilized. Therefore, when mother's milk is drawn out at baby's sleeping time or drawn by another than the baby having a feeble sucking force and further when mother cannot directly feed her baby at her breast because her baby is separated from her, the baby cannot be fed with mother's milk.

In order to overcome the abovementioned disadvantages of the conventional breast pump, the inventor has already developed an improved breast pump, which has been registered under a Japanese utility model reg. No. 1018450. This breast pump can overcome the disadvantages of the conventional one. This improved breast pump comprises two cylinders — an outer and an inner cylinders, and the inner cylinder has two open ends one of which is divergent so as to contact about a teat while the other open end is not provided with anything. The outer cylinder is formed as so-called a container having an open and a closed ends. The inner cylinder is adapted to be inserted into the outer cylinder through the said open end of the latter. The inner and outer cylinders are forming a sliding surface on the outer surface of the former and the inner surface of the latter respectively as in an injector so as to thereby slide with respect to each other.

An injector is adapted to suck liquid into a space negatively pressured by sliding the inner cylinder, while this improved breast pump is adapted to draw out mother's milk by sliding the outer cylinder so as to form a negatively pressured space within the inner cylinder.

Mother's milk drawn out is stored through the open end of the inner cylinder into the outer cylinder. According to this improved breast pump, since mother's milk is drawn out by sliding the outer cylinder as abovementioned, conveniently it is not necessary to release the contact face of the breast pump from mother's breast. Besides, the outer cylinder can be forcedly pulled, thus affording to exert a large drawing force. Further, since the inner cylinder can be pulled away from the outer cylinder so that the two cylinders can be individually sterilized in hot water. Therefore, this breast pump is so sanitary that mother's milk drawn out can be fed to the baby instead of being thrown away.

However, this improved breast pump still has the following problems. As abovementioned, in this improved breast pump, since negative pressure is provided into the inner cylinder by means of the sliding surfaces, the outer surface of the inner cylinder and the inner surface of the outer cylinder are fitted with each other substantially without clearance therebetween. Therefore, if dust is attached to the sliding surfaces or mother's milk settles thereon, the outer cylinder cannot be moved with respect to the inner cylinder, thus failing in milking. By further strongly pulled the inner cylinder and/or the outer cylinder, they are broken. Sliding surfaces are naturally associated with such disadvantages. Further, in order to form such sliding surfaces, the inner and outer cylinder have to be made of glass in general. Otherwise, excellent sliding surfaces from which air does not leak out cannot be obtained. A breast pump made of glass has such difficulties in manufacturing, besides its being very easy to break.

An object of the present invention is, therefore, to provide a new breast pump by which disadvantages resulting from the presence of sliding surfaces can be eliminated.

Another object of the present invention is to provide a breast pump which is not necessarily made of glass but may be made of plastic.

A further object of the present invention is to provide a breast pump in which a packing mounted on an inner cylinder can be easily removed away.

A further object of the present invention is to provide a breast pump in which provided is a means for removably fitting a rubber nipple to the open end of the outer cylinder so that mother's milk drawn out and stored in the outer cylinder can be fed through the said rubber nipple to a baby after pulling away the inner cylinder from the outer cylinder.

A further object of the present invention is to provide a breast pump in which dust or the like is prevented from intruding into a clearance between the outer and inner cylinders when unemployed.

A further object of the present invention is to provide a breast pump in which graduations are provided on the outer cylinder whereby the amounts of milk drawn out and fed can be measured.

A further object of the present invention is to provide a breast pump in which a ring can be mounted for stabilizing a teat.

Further objects of the present invention will be apparent from the following description given with reference to the appended drawings, in which:

FIG. 1 is a front view of a breast pump made of plastic according to the present invention;

FIG. 2 is a longitudinal sectional view of the breast pump of FIG. 1;

FIG. 9 is a front view of an outer cylinder with a rubber nipple mounted thereon; and FIG. 10 is another example of a breast pump made of glass according to the present invention.

As shown in FIGS. 1 and 2, a breast pump according to the present invention comprises an inner cylinder 10 and an outer cylinder 30.

Figure 3:
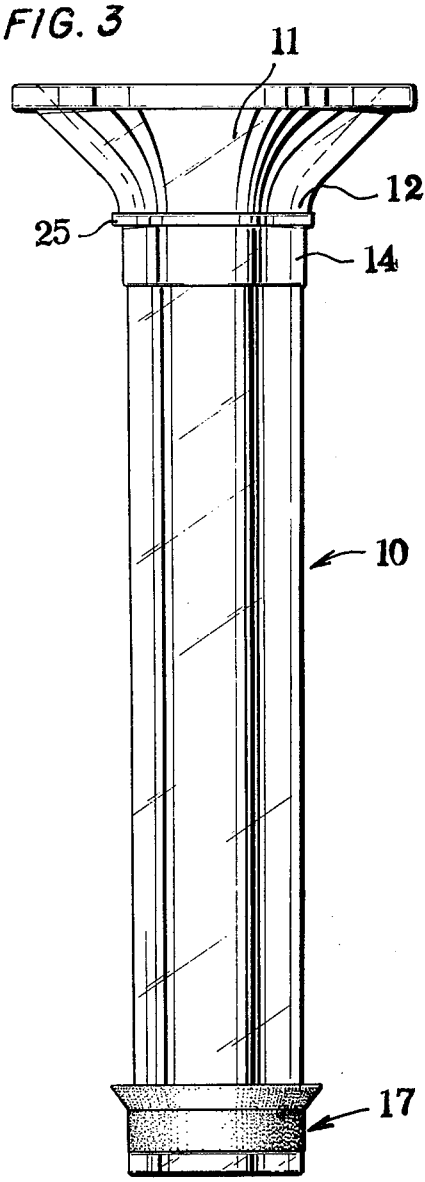
FIG. 3 is a front view of an inner cylinder after pulled away from an outer cylinder.
Figure 4:
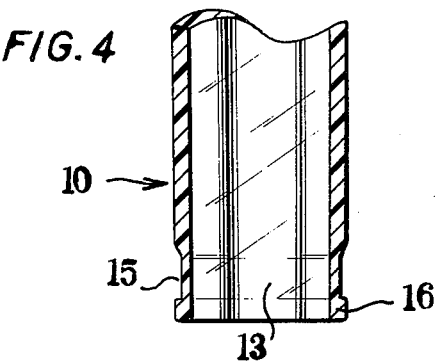
FIG. 4 is a sectional view for illustration of the lower end of the end of the inner cylinder.

The inner cylinder 10 is provided at one open end with a divergent portion 11 adapted to be put against a breast. The inner cylinder is slightly convergent from the narrowest portion 12 of the said divergent portion toward the other open end 13. Such a convergent shape is for the purpose of convenience in taking the inner cylinder out of a mold after molding the same of plastic material. This inner cylinder is molded of a transparent and highly heat-resisting plastic e.g. polycarbonate. An expanded portion 14 as shown in FIG. 3 is provided below the said portion 12. This expanded portion 14 ensures substantially close fitting of the inner cylinder against the inside of the outer cylinder as shown in FIG. 2 and prevents the inner cylinder from shaking. A protrusion 25 is provided over the whole periphery of the inner cylinder at the position slightly above the expanded portion 14. The expanded portion 25 comes in contact with the upper edge of the outer cylinder when the inner cylinder is inserted into the outer cylinder, and hinders the inner cylinders from farther intruding thereinto, thus preventing the damage of the cylinder on account of the contact between the lower edge of the inner cylinder and the inside of the outer cylinder. Further, since the upper edge of the outer cylinder comes substantially into contact with the protrusion 25, dust or the like is prevented from intruding into the clearance between the inner and outer cylinders. As shown in FIG. 4 a channel 15 is provided over the whole outer periphery of the lower open end of the inner cylinder. In the said channel 15 a belowmentioned packing is fitted. In the embodiment as shown in FIG. 4, the channel 15 is formed by recessing the thickness of the inner cylinder, but instead of this, it may be so formed as the thickness of the bottom portion of the recess is substantially the same with that of the portion above this channel.

Below this channel 15 provided is a flange 16 by which the packing is prevented from being released. The outer diameter of the flange 16 is so dimensioned as to be substantially the same with or slightly smaller than the outer diameter of the cylindrical portion of the packing when the latter is fitted into the channel 15.

With the abovementioned arrangement, the packing can be released from the channel and the packing and the inner cylinder can be individually treated in case of e.g. washing and sterilization. It is possible to directly attach a packing to the inner cylinder with paste or other adhesive instead of providing such a channel, but then they can be neither separated from each other thus nor treated individually under the most suitable condition for each of them in case of e.g. washing and sterilization. Further, the part about the contact portion between the inner cylinder and the packing cannot be sufficiently washed, thus possibly causing attached mother's milk to become corrupt. Further, it is difficult to exchange a packing damaged or worn out with a new one.

Figure 5:
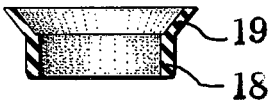
FIG. 5 is a sectional view of a packing.

The packing 17 is formed of natural rubber and includes a cylindrical supporting portion 18 and a divergent contact portion 19 above the former as shown in FIG. 5. The said packing can be made of natural rubber, synthetic rubber e.g. silicone rubber, flourine system resin e.g. poly-4-ethylene-fluoride known under the tradename of "Teflon" or the like. The packing 17 may be otherwise formed e.g. into a simply cylindrical annular ring. However, when the outer cylinder provided with a packing and the inner cylinder are displaced with respect to each other, a packing in a shape like this embodiment can function effectively even if the contact area between the packing and the inside of the outer cylinder is small, and further, a great force is not required for pulling the outer cylinder.

In case of mounting a packing as shown in FIG. 5 on the inner cylinder, the contact portion 19 has to be disposed on the side of the divergent portion 11 of the inner cylinder so as to utilize a valve effect of the contact portion. If it is reversedly disposed, air flows between the outer cylinder and the packing thus failing in effective milking.

Figure 6:
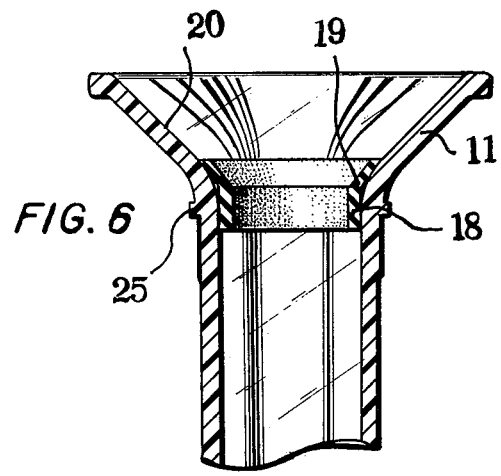
FIG. 6 is a sectional view of an inner cylinder with a teat stabilizing ring having the same size and shape with the packing of FIG. 5 and fitted into the divergent portion of the said inner cylinder.

The inner diameter of the supporting portion of the packing 17 is so dimensioned as to be substantially the same with or slightly smaller than the outer diameter of the said channel 15, while the outer diameter of the largest diametered portion of the contact portion 19 is slightly larger than the inner diameter of the outer cylinder. With this arrangement, the portion of the contact portion 19 larger than the inner diameter of the outer cylinder is curved along the inside surface of the outer cylinder thus affording to hold the two in close contact. For obtaining an effective curve of the contact portion, the thickness of the same is made thinner than that of the supporting portion 18 as seen in FIG. 5. The packing 17 is mounted on the lower end of the inner cylinder in the embodiment as shown in FIGS. 2 and 3, but may be mounted on any other position e.g. on the upper position than this. Further, not one but a plurality of packings may be mounted. Preferably, the outer diameter of the packing 17 is so selected as to be fitted with the inside surface of the divergent portion 11 of the inner cylinder. In other words, by selecting the outer diameter of the supporting portion 18 and the divergent angle of the contact portion 19 so as to closely fit the packing with the inside 20 of the divergent portion 11 as shown in FIG. 6, the packing can be adapted to serve also as a stabilizing ring for stabilizing a teat. In the embodiment of FIG. 6, the outer diameter of the supporting portion 18 is slightly larger than the inner diameter of the parallel part of the inside 20, while the divergent angle of the contact portion 19 is substantially the same with that of the inside 20. Thus, the packing is supported through the resilient force thereof by the inside 20 of the divergent portion. By thus mounting a stabilizing ring on the inside 20 of the diverging portion 11, a teat is preferably supported by this ring without slipping off from the center of the inner cylinder. Besides, by adapting a packing to serve also as a stabilizing ring, the parts of a breast pump can be extremely economically manufactured.

Figure 7:
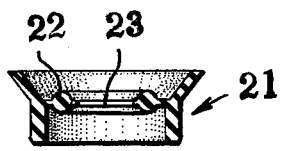
FIG. 7 is a sectional view of another example of a teat stabilizing ring to be applied when a teat is depressed.

Another embodiment of a stabilizing ring is shown in FIG. 7, which can be applied when a teat is depressed into the breast. This ring is provided at the inside thereof with an annular member 22 projecting inwardly so as to make small an opening 23. The inner diameter of the opening 23 is slightly larger that the outer diameter of a teat, so that if a teat is depressed a higher sucking force can be exerted at the opening 23 than in case of the abovementioned ring not having such an annular member, thus achieving effective milking. The other part of this ring 21 is the same with the corresponding part of the said packing 17, and if the annular member is cut away therefrom, the ring 21 can serve as a packing.

Figure 8:
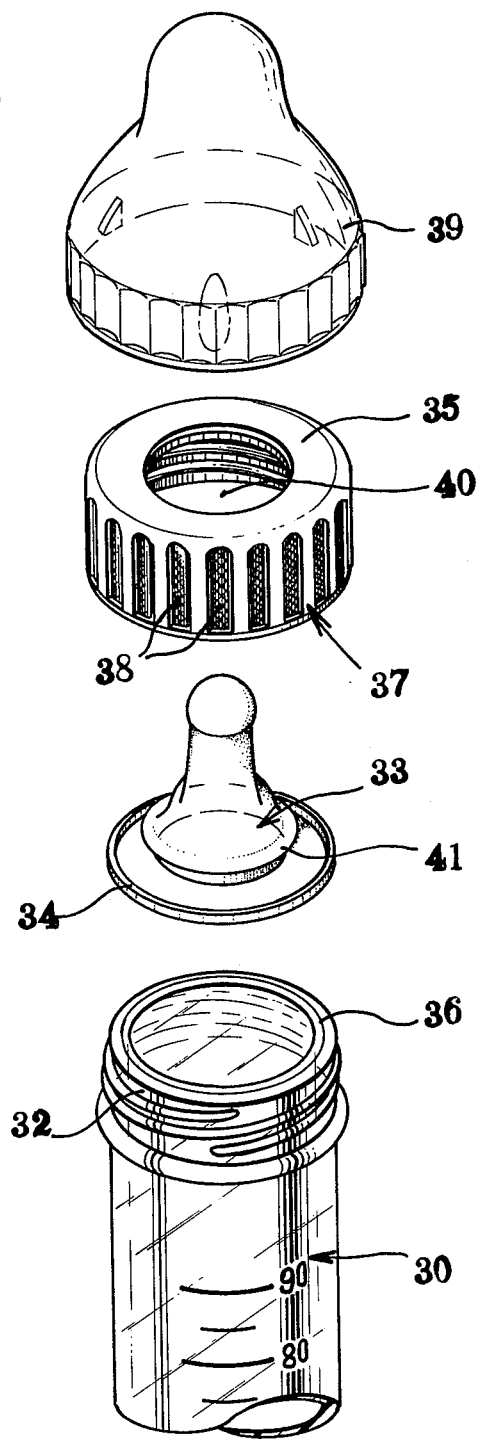
FIG. 8 is a perspective view of a rubber nipple to be mounted on the open end of the outer cylinder after the inner cylinder is pulled away therefrom and a fitting means for the said rubber nipple.

The outer cylinder 30 is, like the inner cylinder, made of highly heat-resisting and transparent plastic e.g. polycarbonate. As shown in FIGS. 1 and 2, the outer cylinder 30 is opened at the upper end and closed at the lower end by a lid 31 thus forming so called a container. Preferably, the contact portion between the wall of the outer cylinder and the lid 31 is formed in a curved shape so as to facilitate washing. On the outside of the open end of the outer cylinder provided is a means 32 for removably mounting a rubber nipple 33 as shown in FIG. 8. In this embodiment, the said means 32 comprises an external thread which is adapted to be engaged with an internal thread provided on the inside of a socket 37 which holds the peripheral edge 34 of the rubber nipple between an upper plate 35 of the socket and the edge 36 of the open end of the outer cylinder. This means 32 may be formed by providing a channel over the whole outer peripheral surfac of the outer cylinder. Then, the rubber nipple is provided with a projection adapted to be fitted into the said channel whereby the rubber nipple is secured to the outer cylinder. The said means 32 comprising a thread as in this embodiment is advantageous in the following points.

As shown in FIG. 8, a number of vertical shallow channels 38 are provided at regular intervals on the outer peripheral surface of the socket 37. And a required number of projections to be fitted into the said channels 38 are provided on the inside of a cap adapted to be engaged with the socket.

After sterilizing thus formed cap, socket and rubber nipple, the rubber nipple 33 is disposed as projected through an opening 40 of the socket and secured to the latter by engaging a fold 41 with the edge of the upper plate 35. Then, a cap 39 is put over the socket. By this arrangement, in mounting the rubber nipple on the outer cylinder 30, the socket 37 has only to be screwed through the cap 39 into the thread on the outer cylinder, without touching the sterilized portion of the rubber nipple. In FIG. 9, shown is the outer cylinder with the rubber nipple thus mounted thereon.

Below the said means 32, a projection 42 is provided over the whole peripheral surface of the outer cylinder so as to prevent the socket 37 from farther advancing.

On the outer cylinder provided are graduations 43 in the longitudinal direction, by which the amount of mother's milk fed to the baby can be measured.

At the lower end of the outer cylinder, provided is a base 44 integral with the outer cylinder. The base 44 is useful for holding the breast pump in a standing position. However, it is difficult to provide a glass breast pump with such a base and if provided, the cost thereof becomes high, while a plastic one can be easily provided therewith.

In FIG. 10, shown is a breast pump 50 made of glass, in which an inner cylinder 51 is formed similarly to the abovementioned cylinder 10, but an outer cylinder 52 does not have a base or the like portion corresponding to the base 44.

What I claim is:

1. A breast pump comprising an inner cylinder, an outer cylinder, a packing mounted on the outside of said inner cylinder and adapted to seal up a clearance between said inner and outer cylinders, and a stabilizing ring, said inner cylinder having two open ends, one end being divergent so as to be put against a breast and the other end being inserted into said outer cylinder and displaced therein, the outer diameter of said inner cylinder being smaller than the inner diameter of said outer cylinder to permit said displacement of said inner cylinder in said outer cylinder, said outer cylinder being a container with an open end and a closed end, at least one channel being provided over the whole periphery of the outside surface of said inner cylinder into which said packing is removably fitted, said stabilizing ring being mounted on the inside surface of said divergent portion of said inner cylinder for stabilizing a teat.

2. A breast pump as claimed in claim 1, in which provided are a stabilizing ring for ordinary use and another stabilizing ring applicable to a teat depressed into the breast.

3. A breast pump as claimed in claim 1, in which said packing can also serve as a stabilizing ring.

* * * * *